(12) United States Patent
Cho et al.

(10) Patent No.: US 8,492,149 B2
(45) Date of Patent: Jul. 23, 2013

(54) EFFICIENT GENERATION OF NEURAL PROGENITORS, NEURONS, AND DOPAMINERGIC NEURONS FROM HUMAN EMBRYONIC STEM CELLS

(75) Inventors: Myung Soo Cho, Seoul (KR); Myung-Hwa Kim, Gyeonggi-do (KR); Young-II Moon, Gyeonggi-do (KR); Shin Yong Moon, Seoul (KR); Sun Kyung Oh, Seoul (KR); Hee Sun Kim, Seoul (KR); Dong-Wook Kim, Seoul (KR)

(73) Assignee: JE IL Pharmaceutical Co., Ltd., Seoul (KR)

( * ) Notice: Subject to any disclaimer, the term of this patent is extended or adjusted under 35 U.S.C. 154(b) by 866 days.

(21) Appl. No.: 12/303,670

(22) PCT Filed: Jun. 5, 2007

(86) PCT No.: PCT/KR2007/002717
§ 371 (c)(1),
(2), (4) Date: Jan. 30, 2009

(87) PCT Pub. No.: WO2007/142449
PCT Pub. Date: Dec. 13, 2007

(65) Prior Publication Data
US 2010/0317103 A1 Dec. 16, 2010

(30) Foreign Application Priority Data

Jun. 7, 2006 (KR) .................. 10-2006-0050659
Jan. 5, 2007 (KR) .................. 10-2007-0001664

(51) Int. Cl.
C12N 5/00 (2006.01)
C12N 5/02 (2006.01)
C12N 5/071 (2010.01)

(52) U.S. Cl.
USPC ........... 435/377; 435/366; 435/368; 435/383; 435/384

(58) Field of Classification Search
None
See application file for complete search history.

(56) References Cited

U.S. PATENT DOCUMENTS

| 6,833,269 B2 | 12/2004 | Carpenter et al. |
| 2002/0068045 A1 | 6/2002 | Reubinoff et al. |
| 2005/0244964 A1 | 11/2005 | Davidson |
| 2006/0073587 A1 | 4/2006 | Stice et al. |

FOREIGN PATENT DOCUMENTS

WO 2005021720 A2 3/2005

OTHER PUBLICATIONS

JP 2003-533224, 68 pages, with English Abstract.
JP2004-533835A, 66 pages, with English Abstract.
JP2007-503811A, 46 pages, with English Abstract.
Japanese Office Action, Application No. 2009-514200; 4 pages.

*Primary Examiner* — Anne-Marie Falk
(74) *Attorney, Agent, or Firm* — Casimir Jones, S.C.

(57) ABSTRACT

The present invention relates to a method for inducing the differentiation of neural progenitors, neurons, and dopaminergic neurons from human embryonic stem cells with high efficiency, in which neural selection can be performed by the selected media and physical methods. The invention has advantages such as higher efficiency, the effect of lowering cost and time, and maintenance of neural progenitors for a longer period of time, as compared to the known methods for inducing the differentiation into neural progenitors, neurons, and dopaminergic neurons. Accordingly, the method can stably generate cells used for treating Parkinson's disease or other nervous system diseases.

5 Claims, 8 Drawing Sheets

**Normal embryoid bodies
to be selected**

**Cystic embryoid bodies
to be removed**

Neural progenitors cultured after neural selection

Expanded neural progenitors after neural expansion culture

The differentiated neurons express neunal markers, βIII -tubulin and NeuN

The neurons (βIII -tubulin) differentiated from neural progenitors(A2B5) were formed The neurons (βIII -tubulin) differentiated from neural progenitors(Nestin) were formed ES : mRNA of embryonic stem cell colony
EB : mRNA of embryoid body
SNM : mRNA of spherical neural mass
DA : mRNA of final differentiated
      dopaminergic neurons

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
accacagtcc atgccatcac                                               20

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
tccaccaccc tgttgctgt                                                19

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
cgttctcttt ggaaaggtgt tc                                            22

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
acactcggac cacgtctttc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ggcaacctac gcaagatggc                                               20

<210> SEQ ID NO 6
<211> LENGTH: 20
<212> TYPE: DNA
```

<213> ORGANISM: Artificial Sequence
<220> FEATURE:
<223> OTHER INFORMATION: Synthetic

<400> SEQUENCE: 6
tgagggctgt gtctgttcgg                                                     20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
caatgcgggg aggagaagtc                                                     20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ctctggacca aactgtggcg                                                     20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gctaaacaaa acttgcatgc                                                     20

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ctcatatcat gtgccatact ag                                                  22

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ctgggtgtac tgcacacgtt at                                                  22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
tactcgctct cgtctttgtc ct                                                  22

-continued

```
<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gcaggtcgaa cgaagagacg                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
caagtgtgag ctttattggc                                                    20

<210> SEQ ID NO 15
<211> LENGTH: 16
<212> TYPE: DNA
<213> ORGANISM: Artificial Sequence
<220> FEATURE:
<223> OTHER INFORMATION: Synthetic

<400> SEQUENCE: 15
actaggccct acacac                                                        16

<210> SEQ ID NO 16
<211> LENGTH: 17
<212> TYPE: DNA
<213> ORGANISM: Artificial Sequence
<220> FEATURE:
<223> OTHER INFORMATION: Synthetic

<400> SEQUENCE: 16
tttttttgac agtccgc                                                       17
```

EFFICIENT GENERATION OF NEURAL PROGENITORS, NEURONS, AND DOPAMINERGIC NEURONS FROM HUMAN EMBRYONIC STEM CELLS

TECHNICAL FIELD

The present invention relates to a method for efficiently inducing differentiation of neural progenitors, neurons, and functional dopaminergic neurons from human embryonic stem cells. This work was supported by a grant (SC2160) from Stem Cell Research Center of the 21C. Frontier R & D Program funded by the Ministry of Science and Technology.

BACKGROUND ART

Parkinson's disease, which has been known as a refractory disease, is caused by the degeneration of dopaminergic neurons in the substantia nigra of the midbrain. The disease is a fatal geriatric disease, since it frequently occurs and gradually causes chronic movement disorders. Therefore, it is necessary to develop a method for treating the disease. Until now, there have been known treatments such as drug therapy using several drugs, and surgery, which implants a deep brain stimulator. However, drug therapy has short term-effects, including side effects after continuous administration, thereby not being easily applied. Furthermore, surgical therapy for Parkinson's disease imposes physical and economic burdens on the patient. Accordingly, an alternative treatment for Parkinson's disease is absolutely needed.

Recently, cell replacement therapy, in which depleted or damaged cells can be replaced with new healthy ones, has been considered as an effective treatment for the disease. In particular, as studies on human stem cells have rapidly developed, many studies for using the stem cells to restore damaged tissues or cells which are hard to be repaired have been actively conducted widely in several applications. More specifically, since adult stem cells, which are used to restore damaged brain and neural tissues, are hard to obtain and supply, a study has been actively conducted on the differentiation of brain and neural cells from embryonic stem cells. Embryonic stem cells can be isolated from the inner cell mass of the blastocyst during the embryonic development stage, and can proliferate indefinitely in an undifferentiated state under specific culture conditions. Furthermore, since embryonic stem cells are pluripotent, they can differentiate into every cell type according to conditions. Therefore, embryonic stem cells can be a source of cells used in cell therapy of all kinds of the tissues.

Cell replacement therapy for Parkinson's disease has been studied for a long time. However, cell replacement therapy using human embryonic stem cells has lately been studied, and many research institutes worldwide are currently engaged in this research.

The current studies on human embryonic stem cells are described in the following publications:

Human embryonic stem cells were induced to differentiate into neural precursors and various types of neurons (Su-Chun Zhang et al., 2001).

The efficiency of generating dopaminergic neurons was increased by coculturing human embryonic stem cells with PA6 cells and then adding a glial cell derived neurotrophic factor, GDNF (Kimberley et al., University of Colorado, USA, 2004).

It was confirmed that dopaminergic neurons were generated from embryonic stem cell aggregates by coculturing human embryonic stem cells with a stromal cell, PA6 cell, and the dopaminergic neurons generated a dopaminergic neuron specific marker. Unfortunately, it was reported that after transplantation, only a small portion of the cells generated were the dopaminergic neurons, and other type of cells still remained (Zeng et al., National Institute on Drug Abuse, USA, 2004).

Embryonic stem cell aggregates were confirmed to differentiate into dopaminergic neurons in serum-free suspension culture without any other factors, in which the neurons released dopamine to respond electrophysiologically, and even after transplantation, the cells released dopamine (Schulz et al., BresaGen Inc. 2004).

Human embryonic stem cells were induced to form a cluster of neural progenitors using a different stromal cell, MS5 cell, and then various growth factors and differentiation-inducing factors were added, so that 70% or more of the neurons were differentiated into dopaminergic neurons (Perrier et al., Sloan-Kettering Institute, 2004).

A behavior disorder caused by Parkinson's disease was found to be improved, in which neural progenitors derived from human embryonic stem cells were transplanted into a Parkinsonian rat, and the transplanted cells spontaneously were differentiated into dopaminergic neurons (Tamir et al., Hadassah University Hospital, Israel, 2004).

In Korea, there are a few research institutes that are engaged in the study on the differentiation of dopaminergic neurons from human embryonic stem cells. It was published that almost 20% of neurons derived from Human embryonic stem cells were differentiated into dopaminergic neurons with various differentiation-inducing factors, in which function of the differentiated cells and other makers, however, were not be confirmed, the efficiency was lower than that in other publications, and the survival rate after transplantation was not reported (Sepill Park et al., Maria Infertility Hospital, 2004).

Human embryonic stem cells were cocultured with PA6 stromal cells, so as to differentiate into neural progenitors. The neural progenitors were cultured in the form of a spherical neural mass or a single cell with a combination of differentiation factors, thereby differentiating into dopaminergic neurons. Unfortunately, the differentiation efficiency and the result after transplantation were not impressive (Sanghoon Lee, et al., Hanyang University, Korea).

Even though many research institutes worldwide are currently engaged in the research, there are still problems in that the efficiency of generating pure dopaminergic neurons from total cells is very low, and the survival rate and functionality after transplantation have not been improved. Therefore, the present inventors have established a method for obtaining neural progenitors, neurons, and pure dopaminergic neurons from embryonic stem cells with high efficiency of 80% or more, in which the cells at the stage of neural progenitor are subcultured to produce a large number of progenitors, neurons, and dopaminergic neurons, thereby completing the present invention.

DISCLOSURE

Technical Problem

The present invention aims to provide a method for inducing differentiation of neural progenitors, neurons, and functional dopaminergic neurons from embryonic stem cells.

Since there are problems in that differentiation methods known in the art cannot be realized due to their low efficiency, the present invention aims to increase the differentiation efficiency, functionality, and productivity achieved for practical use.

BEST MODE

Figure 1:
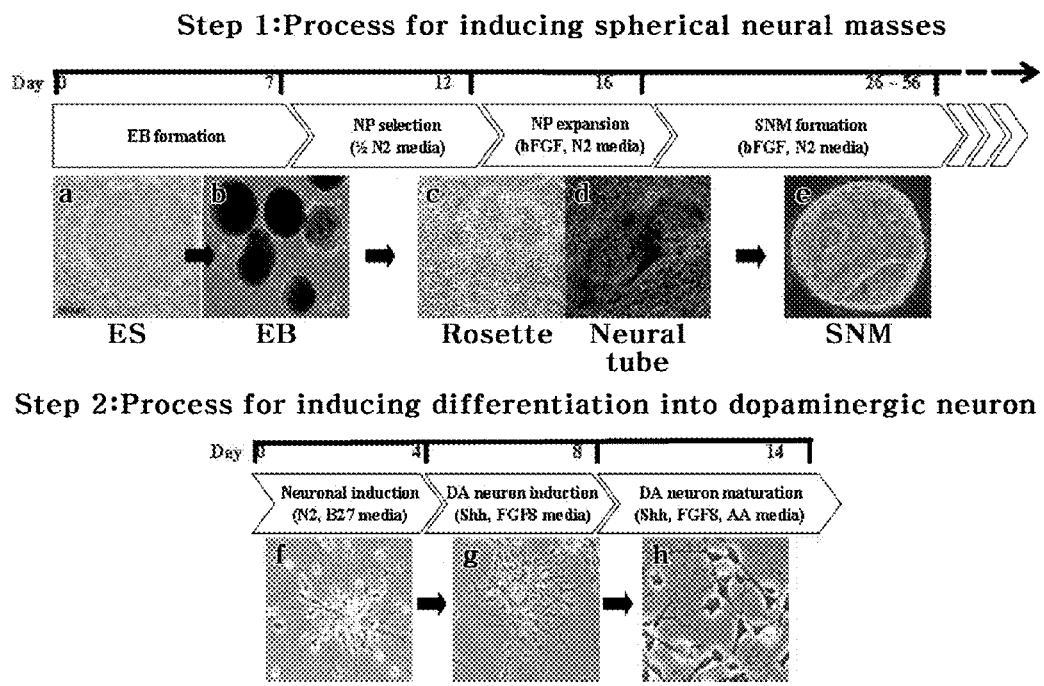
FIG. 1 is a schematic diagram of showing the differentiation of neural progenitors, neurons, and dopaminergic neurons from human embryonic stem cells, in which a in FIG. 1 is a photograph showing the morphological characteristics of embryonic stem cell colonies, b in FIG. 1 is a photograph showing the morphological characteristics of the selected embryoid bodies differentiated from embryonic stem cell colonies, c and d in FIG. 1 are photographs showing the morphological characteristics of neural rosette and neural tube as neural structures produced by neural selection and expansion procedures after EB (embryoid body) formation, e in FIG. 1 is a photograph showing the morphological characteristics of a spherical neural mass produced by suspension-culturing of neural structures mechanically dissected, and f, g, and h in FIG. 1 are photographs showing the morphological characteristics of neurons produced by culturing the spherical neural masses mechanically dissected.

In one embodiment, the present invention relates to a method for efficiently inducing differentiation of neural progenitors, neurons, and functional dopaminergic neurons from human embryonic stem cells. Specifically, the method of the invention comprises steps of:
forming embryoid bodies from human embryonic stem cells, and then removing the cystic embryoid bodies;
primarily, selectively expanding neural cells for differentiation into nervous system;
secondarily, mechanically isolating only neural structures to prepare spherical neural masses;
repeatedly removing structures other than the spherical neural masses during subculturing to prepare spherical neural masses with high purity; and
inducing the differentiation into neurons and dopaminergic neurons in the selected media.

In one specific embodiment, a method for inducing the differentiation of neural progenitors from human embryonic stem cells with high efficiency and purity comprises the steps of
(a) attaching the embryoid bodies cultured for at least 5 to 21 days, in which the cystic embryoid bodies had been removed, to the surface of culture dishes coated with Matrigel®, laminin, or L-polyornithine, and culturing in media containing 0.5×N-2 supplement for at least 5 to 7 days to inhibit the growth of cells other than neural cells;
(b) dissecting and isolating neural structures from cells derived from attached embryoid bodies expanded for at least 3 to 7 days in media containing N-2 and bFGF;
(c) removing spot-forming fibroblast-like cells and cystic structures, which are generated during the procedure of culturing spherical neural masses derived from the dissected and isolated neural structures, and isolating only the expanded neural structures in the spherical neural masses; and
(d) repeating the step (c) at least four times to produce a large number of spherical neural masses with high purity.

The term "embryonic stem cell" as used herein refers to a cell that can be isolated from the inner cell mass of the blastocyst during the embryonic development stage, proliferate indefinitely in an undifferentiated state under specific culture conditions, and differentiate into every cell type according to conditions.

The step (a) is a step for inducing the differentiation of the selected embryoid bodies and spherical neural masses from the embryonic stem cells used in the present invention. More specifically, the step is a step for attaching the differentiated and selected embryoid bodies, which are derived from the embryonic stem cells cultured for a predetermined period of time, to the surface of culture dishes coated with one of Matrigel®, laminin, or L-polyornithine to culture, and culturing the embryoid bodies in the media containing 0.5×N-2 supplement in order to selectively induce the survival and division of neural precursors. The neural precursors selectively survive due to the media containing Matrigel®, laminin, or L-polyornithine, and 0.5×N-2.

The step (b) is a step for culturing the cells derived from the embryoid bodies, which are selected and cultured in the step (a), that is, the neural precursors in the specific media for 3 to 5 days, and dissecting and isolating the neuronal structures from the neural precursors. After the expansion of the selected cells and formation of the spherical neural masses, the cells are subcultured in the media containing 1×N-2 and 20 ng/ml basic fibroblast growth factor (bFGF). The desirable spherical neural masses can be selectively cultured after the steps (a) and (b).

The neural structures of the invention refer to structures having neural rosettes or neural tube-like morphologies.

The dissection method used in the invention is a method for dissecting only the neural structures from the spherical neural masses, and can be performed by the various methods known in the art. In the specific Example of the invention, the dissection method is preferably a mechanical method, in particular, a mechanical method using a glass Pasteur pipette. The mechanical method using a glass Pasteur pipette is a method for dissecting a desired region with the Pasteur pipette, which is heated and drawn thin similar to the size of a thickness of a hair, under a microscope.

The steps (c) and (d) are a step for expanding and culturing only the spherical neural masses having the neural structures isolated in the step (b). That is, the spherical neural masses prepared in the steps are dissected into small pieces of 5 to 8 by the dissection method, preferably the mechanical method, and then can be expanded in the media containing 1×N-2 and bFGF for 1 to 2 weeks. The process is repeated for a predetermined passage or more, preferably for 4 passages or more, more preferably for 4 to 10 passages, so that a large number of spherical neural masses can be produced with high purity, without losing their differentiation capability.

The media used in the steps (a) to (d) can be hESC (human embryonic stem cell) culture media, preferably DMEM/F12 containing 2 mM L-glutamine, 1% non essential amino acid and 0.5% penicillin-streptomycin (P/S), and/or 0.1 mM β-mercaptoethanol. In the specific embodiment of the invention, the DMEM/F12 media containing 0.1 mM β-mercaptoethanol were used.

In another specific embodiment, the present invention relates to a method for inducing the differentiation into neurons, in which the neural progenitors prepared in the method are isolated to culture in the media containing N-2 and bFGF for 1 to 2 days, and further cultured in the media containing N-2 and B27 for 3 to 7 days.

In the method, upon isolating and culturing the neural progenitors, the neural progenitors are dissected and separated by the mechanical method using the glass Pasteur pipette, not a chemical method, so as to ensure improvement in survival rate, and the neural progenitors are primarily cultured in the specific media containing N-2 and bFGF, secondarily cultured in the specific media containing N-2 and B27 for a predetermined period of time, so as to induce the differentiation into neuron with high efficiency.

The specific media can be hESC (human embryonic stem cell) culture media, preferably DMEM/F12 containing 20% knockout serum replacement (K/SR), 2 mM L-glutamine, 1% non essential amino acid and 0.5% penicillin-streptomycin (P/S), and/or 0.1 mM β-mercaptoethanol.

In still another embodiment, the present invention relates to a method for inducing the differentiation into dopaminergic neurons, in which the neurons differentiated by the method were treated with SHH (sonic hedgehog) and FGF8 (fibroblast growth factor 8), cultured for 2 to 4 days, further added with SHH, FGF8, and ascorbic acid (AA), and then cultured for 3 to 7 days.

The differentiation of the dopaminergic neurons from the neurons can be efficiently induced by the method. The hESC (human embryonic stem cell) media can be used, preferably DMEM/F12 containing 20% knockout serum replacement (K/SR), 2 mM L-glutamine, 1% non essential amino acid and 0.5% penicillin-streptomycin (P/S), and/or 0.1 mM β-mercaptoethanol.

In still another embodiment, the present invention further relates to differentiated cells and/or progenies thereof by the method for inducing the differentiation of the human embryonic stem cells.

The present inventors were able to confirm expression of nestin (a marker for neural progenitor), co-expression of βIII-tubulin and NeuN (neuronal markers), co-expression of βIII-tubulin and A2B5, co-expression of βIII-tubulin and nestin, an action potential specific to neuronal membrane (−60 mV to 20 mV), co-expression of βIII-tubulin and synaptophysin (SYP), and dopamine release into the culture media, in the case of inducing the differentiation of neural progenitors and neurons from human embryonic stem cells by the method of the invention. Accordingly, the differentiated cells and/or the progenies thereof according to the invention can have various properties including the expression of nestin (a marker for neural progenitor); the co-expression of βIII-tubulin and NeuN (neuronal markers); the co-expression of βIII-tubulin and A2B5; the co-expression of βIII-tubulin and nestin; the action potential specific to neuronal membrane (−60 mV to 20 mV); the co-expression of βIII-tubulin and synaptophysin (SYP); and dopamine release into the culture media.

The properties of the differentiated neural progenitors or neurons induced according to the method can be confirmed by the method known to those skilled in the art, such as RT-PCR assessing mRNA levels of the genes encoding the proteins or immunostaining against the proteins. The more properties the cells include from the above-listed, the higher probabilities the cells can be characterized as the neural progenitor or neuron. The cells and/or the progenies thereof have three or more properties, preferably four or more properties, and more preferably five or more properties. It is preferable that about 40%, 60%, 80%, 90%, 95%, or 98% or more of the differentiated cells induced by the method of the invention are the cells having the desired properties, and higher numerical value is more preferable.

Further, the present inventors were able to confirm co-expression of βIII-tubulin and TH (tyrosine hydroxylase) (markers for dopaminergic neuron), co-expression of TH and AADC (aromatic amino acid decarboxylase), co-expression of TH and En 1 (Engrailed-1), reduction or absence in co-expression of TH and PNMT, reduction or absence in co-expression of TH and DbH (1,3-dibromo-5,5-dimethylhydantoin), reduction or absence in co-expression of TH and GABA (ϒ-aminobutyric acid), expression of Pax6, Sox1, and/or Nurr1 in the spherical neural mass (SNM), reduction or absence in expression of Oct4, En1, Ptx3, and/or DBH in the spherical neural mass (SNM), and reduction or absence in expression of Oct4, DBH in the dopaminergic neuron (DA), in the case of inducing the differentiation of dopaminergic neurons from human embryonic stem cells by the method of the invention.

Accordingly, the differentiated cells and/or the progenies thereof in the invention can have various properties including co-expression of βIII-tubulin and TH; co-expression of TH and AADC; co-expression of TH and En 1; reduction or absence in co-expression of TH and PNMT (phentolamine N-methyl transferase); reduction or absence in co-expression of TH and DbH; reduction or absence in co-expression of TH and GABA; expression of Pax6, Sox1, and/or Nurr1 in the spherical neural mass (SNM), reduction or absence in expression of Oct4, En1, Ptx3, and/or DBH in the spherical neural mass (SNM), and reduction or absence in expression of Oct4, DBH in the dopaminergic neuron (DA).

The properties of the differentiated dopaminergic neurons induced according to the method can be confirmed by the method known to those skilled in the art, such as RT-PCR assessing mRNA levels of the genes encoding the proteins or antibodies against the proteins. The more properties the cells include from the above-listed, the higher probabilities the cells can be characterized as the dopaminergic neuron. The cells and/or the progenies thereof have four or more properties, preferably five or more properties, and more preferably 370 seven or more properties. It is preferable that about 40%, 60%, 80%, 90%, 95%, or 98% or more of the differentiated cells induced by the method of the invention are the cells having the desired properties, and higher numerical value is more preferable.

In still another embodiment, the present invention relates to a therapeutic composition for brain or nervous system diseases comprising the differentiated cells and/or progenies thereof provided by the method of the invention, in particular, neural progenitors, neurons and/or functional dopaminergic neurons.

The neural progenitor prepared in the present invention refers to a cell that has markers for neural progenitor and produces neurons after differentiation. The neuron in the invention refers to a cell having neuronal markers and neuron-specific electrophysiological properties. The dopaminergic neuron refers to a cell that has markers for dopaminergic neuron, releases dopamine into the medium, and recovers its function after transplantation in an animal model.

The brain or nervous system disease means a disease caused by disorder or dysfunction of a nervous system, such as Parkinson's disease, neuralgia, arthritis, a headache, schizophrenia, epilepsy, a stroke, insomnia, dementia, depression, dyskinesia, Alzheimer's disease, dementia with Lewy bodies, Huntington's disease, Tourette's syndrome, anxiety, learning and memory disorder, and neurodegenerative disease. In the specific embodiment of the invention, it was confirmed that the composition of the invention can be usefully applied to treat Parkinson's disease, which is a disease of the nervous system.

The therapeutic composition of the invention may be prepared into a suitable preparation comprising a pharmaceutically acceptable carrier according to the administration route. The preparations suitable for the administration route are disclosed in the art, and may include an agent capable of facilitating membrane permeability.

Further, the therapeutic composition of the invention may be used in a conventional form of medicine. For parenteral preparation, the pharmaceutical composition may be formulated into sterile aqueous solutions, non-aqueous solutions, suspensions, emulsions, or lyophilized preparations. For oral administration, the pharmaceutical composition may be formulated into tablets, troches, capsules, elixirs, suspensions, syrups or wafers. For injectable preparations, the pharmaceutical composition may be formulated into a unit dosage form, such an ampule as a single-dose dosage form or as a multidose container. Further, the therapeutic composition of the invention may be administered with a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent.

Further, a method for treating the brain or nervous system disease using the therapeutic composition of the invention can be administered using a general administration route, which is suitable for the patients with the disease. Examples of the administration route include intraperitoneal, intravenous, intramuscular, subcutaneous, intradermal, oral, topical, nasal, intrapulmonary, and rectal, but are not limited thereto. For oral administration, in order to prevent the cells from digesting, the active ingredient is preferably coated, or the composition is preferably formulated.

Further, the pharmaceutical composition can be administered by any device capable of delivering the active ingredient to the target cell. The preferred administration route and preparation are intravenous injection, subcutaneous injection, intradermal injection, intramuscular injection, drip injection or the like. The injectable preparation can be formulated using an aqueous solution such as saline solution or Ringer's solution, and a non-aqueous solution such as vegetable oil, higher fatty acid ester (for example, ethyl oleate), and alcohols (for example, ethanol, benzylalcohol, propyleneglycol, or glycerine). Further, the injectable preparation may contain a pharmaceutically acceptable carrier such as a stabilizer to prevent degradation (for example, ascorbic acid, sodium bisulfite, sodium pyrosulfite, BHA, tocopherol, and EDTA), an emulsifier, a buffering agent to adjust pH, and an antimicrobial preservative (for example, phenylmercuric nitrate, thimerosal, benzalkonium chloride, phenol, cresol, and benzylalcohol). Preferably, a method for treating a brain or nervous system disease using the therapeutic composition of the invention comprises a pharmaceutically effective amount of the therapeutic composition of the invention. The pharmaceutically effective amount can be easily determined by those skilled in the art, depending on various factors well-known in the medical field, including the type of disease, the age, weight, health condition, sex, and sensitivity to the drug of a patient, administration route, administration frequency, treatment time, and a drug to be blended or combined in use.

Hereinafter, the present invention will be described in more detail with reference to Examples. However, these Examples are for the illustrative purpose only, and the invention is not intended to be limited by these Examples.

MODE FOR INVENTION

Example 1

Culture of Human Embryonic Stem Cell

In order to subculture and maintain undifferentiated human embryonic stem cell lines (SNUhES1, SNUhES3, SNUhES16), the undifferentiated embryonic stem cells were cultured on feeder cells (mouse embryonic fibroblast cell line, ST0), which had been treated with mitomycin-C. DMEM/F12 media containing 20% knockout serum replacement (SR), 2 mM L-glutamine, 0.4 ng/ml basic fibroblast growth factor (bFGF), 1% non essential amino acids (NEAA), 0.5% penicillin-streptomycin, and 0.1 mM β-mercaptoethanol were used as a culture medium. After culturing for 7 days, the expanded embryonic stem cells were mechanically dissociated (a in FIG. 1) into clusters having 200 to 300 cells. Then, the clusters were placed on fresh feeder cells to culture.

Example 2

Differentiation into Neural Progenitor

Figure 2:
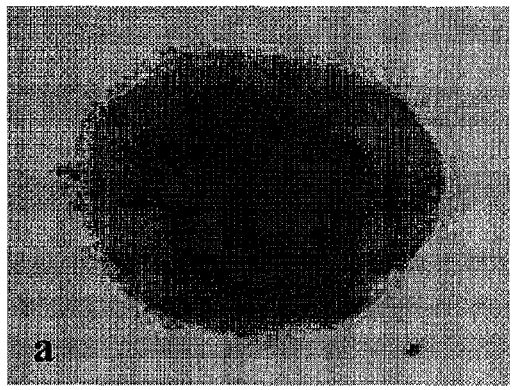
FIG. 2 is a photograph showing the morphological characteristics of embryoid bodies produced by suspension-culturing human embryonic stem cell colonies.
Figure 2:
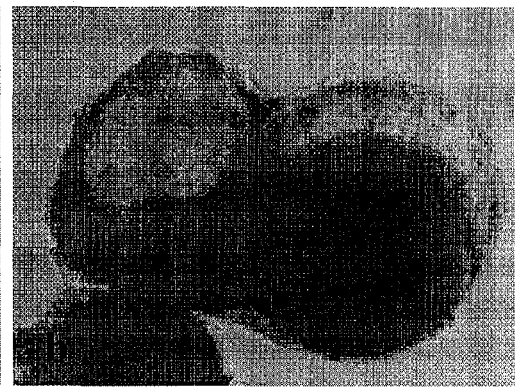
Figure 3:
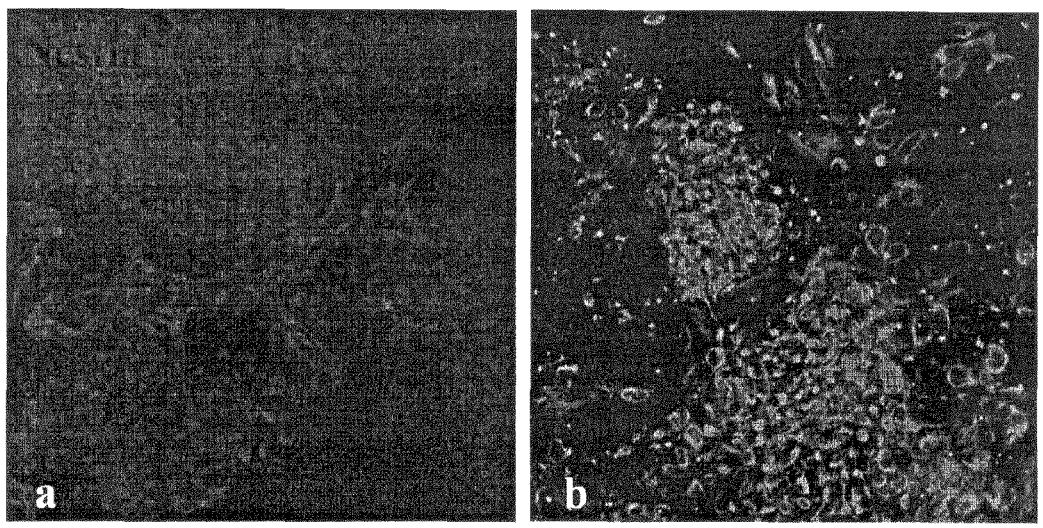
FIG. 3 is a photograph showing the result of immunofluorescence assay, in which the expanded cells selectively produced from the embryoid bodies in attached culture express specific markers to neural progenitors.

The embryonic stem cell colonies were treated with 2 mg/ml collagenase IV; (Invitrogen, Carlsbad, Calif., USA) at 37° C. for 40 minutes, and detached. Then, the cells were put into cell culture dishes, and grown in suspension culture with bFGF-free culture medium, so as to generate embryoid bodies (EB) (b in FIG. 1). The cystic embryoid bodies having a blastula-like structure (b in FIG. 2) were removed. Subsequently, the rest of the embryoid bodies were attached to the surface of culture dishes, which had been coated with Matrigel®(BD, Franklin lakes, NJ, USA), and cultured in ES cell media (without SR and bFGF) containing 1×N-2 supplements for 5 days to selectively culture neural precursors. Then, the neural precursors were cultured in the ES cell media (without SR) containing 1×N-2 supplement and bFGF (20 ng/ml) for 4 days to expand (FIG. 3).

As a result, expression of nestin, which is a neural progenitor marker, was confirmed. Neural structures consisting of the expanded neural precursors (neural rosette, neural tube) (c and d in FIG. 1) were mechanically dissociated with a fire-polished Pasteur pipette, and cultured in the same medium for 1 week to form spherical neural masses. While the spherical neural masses were subcultured three to four times at an interval of 1 week, the well formed spherical neural masses were selected (e in FIG. 1). The selected spherical neural masses were mechanically fragmented into 4 to 8 pieces with the tool described above, and subcultured to expand.

Example 3

Differentiation into Mature Neuron

Figure 4:
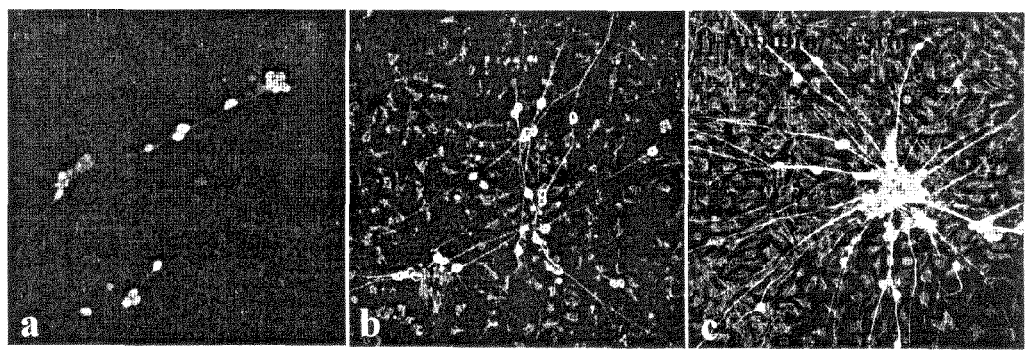
FIG. 4 is a photograph showing the result of immunofluorescence assay, in which the cells differentiated from the human embryonic stem cells express neuronal markers.

The selected spherical neural masses were mechanically dissected into 30 to 80 small pieces, and then put into the 35 mm culture dishes, which had been coated with Matrigel® (50 ug/ml). Subsequently, the spheres were cultured in the media supplemented with 1×N-2 and bFGF (20 ng/ml) for 1 to 2 days, and in the DMEM/F12 media supplemented with 1×N-2, 1×B27 (Gibco) for 4 days, to induce differentiation into neurons having neurites (f in FIG. 1, and FIG. 4). Consequently, it was found that the cells co-express βIII-tubulin and NeuN, co-express βIII-tubulin and A2B5, and co-express βIII-tubulin and nestin as neuronal markers.

Example 4

Confirmation of Functional Neuron

In order to confirm whether the differentiated neurons are biologically functional, neuron-specific electrophysiological properties and the expression of a material involved in secretion of neurotransmitters were observed.

In order to confirm the neuron-specific electrophysiological properties, a "dialyzed" whole-cell recording technique was used to measure the action potential of the membrane. As a result, the cells differentiated by the method of the invention were found to have the action potential of −60 mV to 20 mV (a in FIG. 5).

Figure 5:
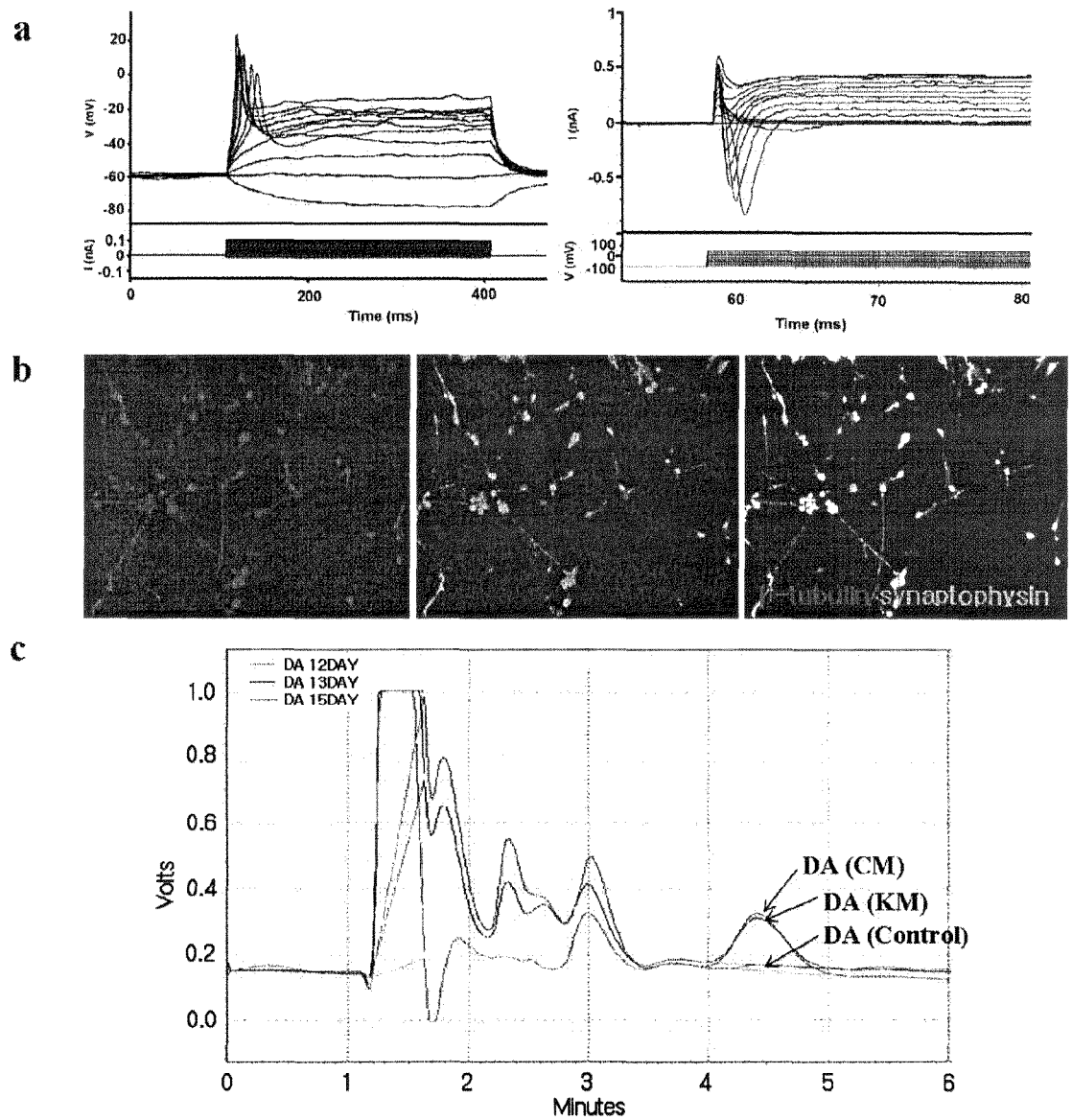
FIG. 5 is a drawing showing the result of confirming whether the differentiated neurons has neuron-specific electrophysiological properties and expresses a material involved in secretion of neurotransmitters, or release dopamine as a dopaminergic neuron for their functional analysis, in which a in FIG. 5 is a drawing showing the result of measuring the action potential specific to neuronal membrane, b in FIG. 5 is a photograph showing the expression of synaptophysin (SYP), which is a neuron-specific protein involved in synapse formation, and c in FIG. 5 is a drawing showing the results of confirming release of dopamine into the media.

Further, an immunofluorescence assay was performed using an antibody against synaptophysin, which is a neuron-specific protein involved in synapse formation, and co-expression of βIII-tubulin and synaptophysin was confirmed (b in FIG. 5)

Further, the dopaminergic neurons were analyzed for the production and release of dopamine. The 24 hr-cultured media was prepared at differentiation day 14 and cells were then treated with 50 mM KCl. From these samples, dopamine levels were assayed by reverse-phase HPLC.

As a result, it was confirmed that dopamine was actually released into the conditioned media (c in FIG. 5).

Based on the above results, the differentiated cells induced by the method of the invention were found to have neuronal properties.

Example 5

Differentiation into Dopaminergic Neuron

Figure 6:
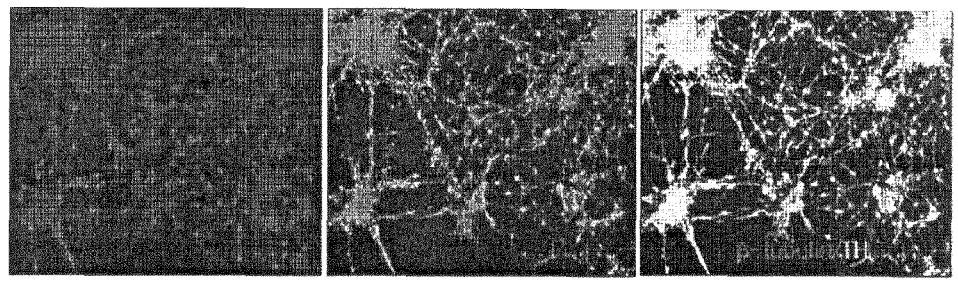
FIG. 6 is a photograph showing the result of immunofluorescence assay, in which most of the differentiated neurons from the human embryonic stem cells co-express tyrosine hydroxylase (TH), which is a marker for dopaminergic neuron.

The neurons prepared by the same process as in Examples 1 to 3 were treated with sonic hedgehog ((SHH), 200 ng/ml; R&D) and fibroblast growth factor 8 (FGF8, 100 ng/ml; Peprotech, Rocky Hill, N.J., USA), and cultured for 4 days. Then, SHH, FGF8, and ascorbic acid (200 uM; Sigma) were added thereto, and further cultured for 6 days to induce differentiation into dopaminergic neurons. As a result, TH (dopaminergic neuronal marker) and βIII-tubulin were found to co-express (FIG. 6).

Example 6

Figure 7:
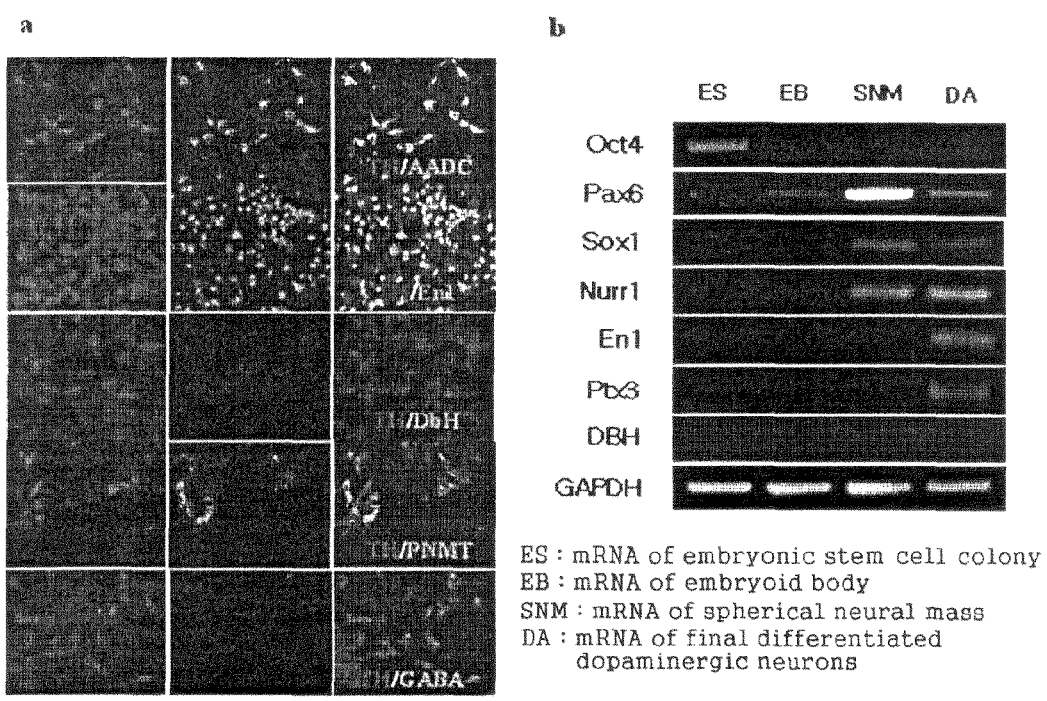
FIG. 7 is a photograph showing the result of immunofluorescence assay and RT-PCR (reverse transcriptase-PCR), in which a in FIG. 7 shows that most tyrosine hydroxylase (TH)-expressing cells express other markers for dopaminergic neuron (AADC, En1), and only a few tyrosine hydroxylase (TH)-expressing cells express a marker for adrenergic neurons (PNMT), a marker for noradrenergic neuron (DbH), or a marker for GABA neurons (GABA), and b in FIG. 7 shows the expression pattern of an undifferentiated embryonic stem cell marker (Oct-4), neural markers (Pax6, Sox1), markers for dopaminergic neuron (Nurr1, En1, Ptx3), and a marker for noradrenergic neuron (DbH) by RT-PCR using mRNA obtained from the cells at each differentiation stage.

Confirmation of Presence, Efficiency, and Functionality of Neurons and Dopaminergic Neurons Immunocytochemistry was performed using antibodies against neuronal markers and specific markers for various catecholaminergic neurons. The results confirmed co-expression of TH and AADC, co-expression of TH and En 1, reduction or absence in co-expression of TH and PNMT, reduction or absence in co-expression of TH and DbH, and reduction or absence in co-expression of TH and GABA (a in FIG. 7).

Further, in order to confirm whether the differentiated cells from human embryonic stem cells express various dopaminergic neuronal markers, RT-PCR (reverse transcriptase-PCR) was performed. RT-PCR using mRNA of neural progenitor (SNM) resulted in expression of Pax6, Sox1, and Nurr1, reduction or absence in expression of Oct4, En1, Ptx3, and DbH. RT-PCR was performed using mRNA of the final differentiated dopaminergic neuron (DA) by the method of the invention. As a result, expression of Pax6, Sox1, Nurr1, En1, and Ptx3, and reduction or absence in expression of Oct4 and DbH were confirmed (a in FIG. 7).

Based on the above results, the differentiated cells induced by the method of the invention were found to have properties of dopaminergic neurons.

Figure 8:
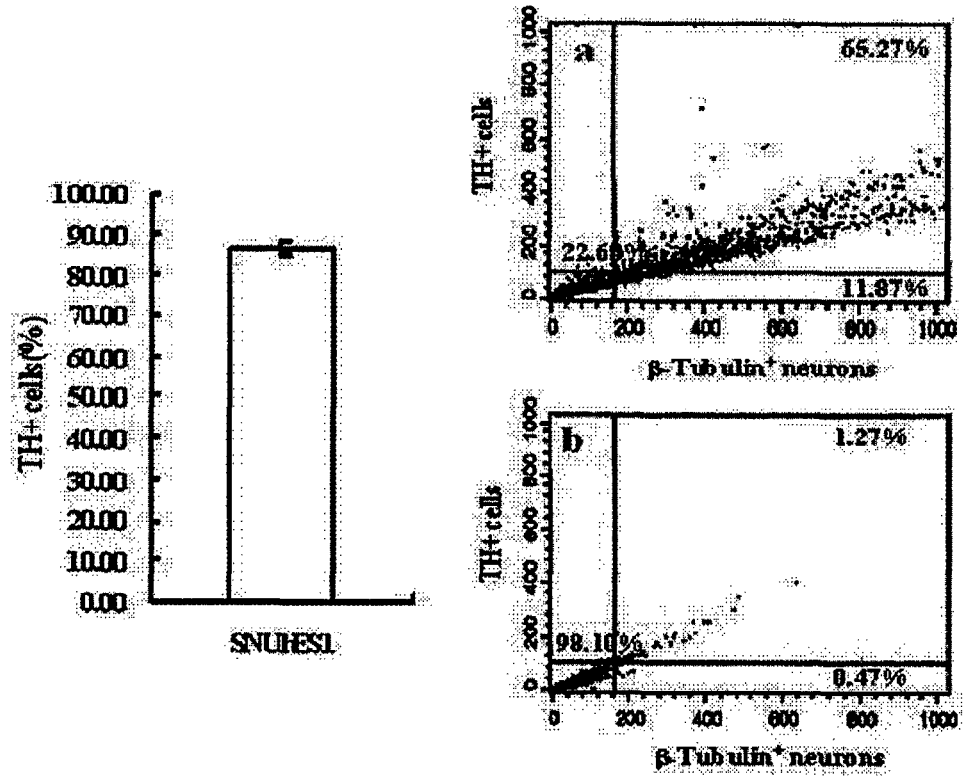
FIG. 8 is a graph showing the result of analyzing the expression ratio of the cells, which co-express the neuronal marker and the marker for dopaminergic neuron, using a fluorescent microscope and flow cytometry, in order to analyze the differentiation of the neurons, which were differentiated into dopaminergic neurons from human embryonic stem cells.

In order to compare the differentiation efficiency of the differentiated neurons into dopaminergic neurons, the neurons were obtained from a group treated with SHH and FGF8 (left graph and right graph a in FIG. 8) and a group not treated with SHH and FGF8 (right graph b in FIG. 8), and labeled with antibodies against a dopaminergic neuron specific enzyme (anti-TH antibody). Then, the labeled neurons were immunocytochemically stained. Using a confocal microscope, the ratio of the positive cells stained was measured. It was found that 86% or more of the cells were differentiated into dopaminergic neurons (left graph in FIG. 8). The ratio of the cells co-expressing βIII-tubulin (neuronal marker) and TH (dopaminergic neuronal marker) was measured with Fluorescence Flow Cytometry (FACS). As a result, 84% or more of the cells was found to differentiate into dopaminergic neurons, which is in consistent with the result of immunocytochemical assay (right graphs in FIG. 8). Based on the above results, it was confirmed that the neural progenitors were differentiated into neurons, in particular, dopaminergic neurons, whereby they can be used to prepare a therapeutic composition for treating diseases in the brain or nervous system.

Example 7

Immunocytochemical Assay, RT-PCR Conditions, and Fluorescence Flow Cytometry 7-1. Immunocytochemical Assay The samples were sequentially fixed with 80%-, 90%-, and 100% ethanol for 10 minutes each, and soaked in water for 10 minutes. Then, the samples were stored in a phosphate buffer solution, or after treatment with 3% formalin solution for 20 minutes, the samples were stored in a phosphate buffer solution. The samples were treated with a blocking solution (2% bovine serum albumin, Sigma) for 1 day, prior to treatment of antibodies, and reacted with primary antibodies for 1 hour and secondary antibodies for 1 hour. Then, the samples were sealed with a fluorescent preservative solution, and observed using a confocal microscope (Nikon, Japan).

The primary antibodies used in the immunocytochemical assay are as follows: Mouse anti-human nestin (1:200), mouse anti-βIII-tubulin:antibody (1:100), mouse anti-mammalian gamma-aminobutyric acid (GABA, 1:100), mouse anti-synaptophysin (1:100), mouse anti-TH (1:200), mouse anti-A2B5(1:100), rabbit anti-phenylethanolamine N-methyl transferase (PNMT, 1:200), rabbit anti-aromatic amino acid decarboxylase (AADC, 1:1000), mouse anti-neuron-specific nuclear protein (NeuN, 1:100), sheep anti-dopamine hydroxylase (DBH, 1:400), mouse anti-human nuclei (1:50), mouse anti-human mitochondria (1:50) (available from Chemicon, Temecula, Calif., USA); goat anti-TH (1:200) (available from Santacruz, Santa Cruz, Calif., USA); rabbit anti-TH (1:500), rabbit anti-vesicular monoamine transporter 2 (VMAT2, 1:500) (available from Pel-Freez); mouse anti-En1 antibody (1:50) (available from Developmental Studies Hybridoma Bank, Iowa City, Iowa. USA).

The secondary antibodies against the primary antibodies used are as follows: Alexa Fluor® 488 donkey anti-mouse IgG, Alexa Fluor® 488 donkey anti-rabbit IgG, Alexa Fluor® 594 donkey anti-mouse IgG, Alexa Fluor® 594 donkey anti-rabbit IgG, Alexa Fluor® 594 donkey anti-goat IgG (1:200) (available from Molecular Probes, Eugene, Oreg., USA), and fluorescein isothiocyanate (FITC)-conjugated rabbit anti-sheep IgG (1:100) (available from Chemicon).

7-2. RT-PCR Conditions

In order to analyze the expression at the level of transcription, RT-PCR was performed as follows.

RNA was isolated from the cells using RNAeasy Kit™ (Trizol (invitrogen)) according to the manufacturer's instructions, and the final products were treated with DNase to remove genomic DNA contamination. RNA guard (Pharmacia Upjohn), DNAse I (Pharmacia Upjohn), and the extracted RNA were added to a buffer solution containing 10 mM Tris buffer (pH 7.5), 10 mM $MgCl_2$, and 5 mM DDT, and then reacted for 30 to 45 minutes at 37° C. In order to remove proteins from the resultant, the phenol chloroform extraction was performed, and RNA was precipitated with 3 M sodium acetate and 100% cold ethanol. The precipitated RNA pellet was washed with 70% ethanol, air-dried, and resuspended in DEPC-treated water.

For reverse transcription, 1 μg of the total RNA was mixed with the final concentration of 1×First Strand Buffer (Gibco), 20 mM DDT, and 25 μg/mL random hexamer (Pharmacia Upjohn). The RNA was denaturated at 70° C. for 10 minutes, and annealed at room temperature for 10 minutes, dNTP was added to a final concentration of 1 mM together with 0.5 it of Superscript II RT (Gibco), reacted at 42° C. for 50 minutes, and heat-inactivated at 80° C. for 10 minutes. Subsequently, for PCR analysis, the sample was stored at −20° C.

The standard PCR was performed using primers specific to the target markers in the following reaction mixture. The selected markers and primer sequences are shown in the following Table 1: cDNA 1.0 pt, 10×PCR buffer (Gibco) 2.5 μl, 10×$MgCl_2$ 2.5 μl, 2.5 mM dNTP 3.0 μl, 5 μM 3' primer 1.0 μl, 5 μM 5' primer 1.0 μl, Taq 0.4 μl, DEPC-treated water 13.6 μl.

TABLE 1

| Gene | Direction of gene | Base sequence | Size of product |
|------|-------------------|---------------|-----------------|
| Gapdh | Forward | 5'-ACCACAGTCCATGCCATCAC-3' (SEQ ID NO: 1) | 450 bp |
|  | Reverse | 5'-TCCACCACCCTGTTGCTGT-3 (SEQ ID NO: 2) |  |
| Oct3/4 | Forward | 5'-CGTTCTCTTTGGAAAGGTGT TC-3' (SEQ ID NO: 3) | 320 bp |
|  | Reverse | 5'-ACACTCGGACCACGTCTTTC-3' (SEQ ID NO: 4) |  |
| Fax6 | Forward | 5'-GGCAACCTACGCAAGATGGC-3' (SEQ ID NO: 5) | 459 bp |
|  | Reverse | 5'-TGAGGGCTGTGTCTGTTCGG-3' (SEQ ID NO: 6) |  |
| Sox1 | Forward | 5'-CAATGCGGGGAGGAGAAGTC-3' (SEQ ID NO: 7) | 464 bp |
|  | Reverse | 5'-CTCTGGACCAAACTGTGGCG-3' (SEQ ID NO: 8) |  |
| Nurr1 | Forward | 5'-GCTAAACAAAACTTGCATGC-3' (SEQ ID NO: 9) | 208 bp |
|  | Reverse | 5'-CTCATATCATGTGCCATACT AG-3' (SEQ ID NO: 10) |  |
| En1 | Forward | 5'-CTGGGTGTACTGCACACGTT AT-3' (SEQ ID NO: 11) | 357 bp |
|  | Reverse | 5'-TACTCGCTCTCGTCTTTGTC CT-3' (SEQ ID NO: 12) |  |
| Dbh | Forward | 5'-GCAGGTCGAACGAAGAGACG-3' (SEQ ID NO: 13) | 197 bp |
|  | Reverse | 5'-CAAGTGTGAGCTTTATTGGC-3' (SEQ ID NO: 14) |  |

TABLE 1-continued

| Gene | Direction of gene | Base sequence | Size of product |
|---|---|---|---|
| Ptix3 | Forward | 5'-ACTAGGCCCTACACAC-3' (SEQ ID NO: 15) | 160 bp |
|  | Reverse | 5'-TTTTTTTGACAGTCCGC-3' (SEQ ID NO: 16) |  |

7-3. Fluorescence Flow Cytometry

The differentiation efficiency of neural progenitors, neurons, dopaminergic neurons from human embryonic stem cells was determined using a flow cytometry. For detection of the neural progenitors, neurons, and dopaminergic neurons, a nestin antibody, a βIII-tubulin antibody, and a tyrosine hydroxylase (TH) antibody were used, respectively. Each cell was washed with a phosphate buffer, treated with 0.05% trypsin/0.1% EDTA (invitrogen) at 37° C. for 5 minutes, and dissociated into single cells. In the case where the antigen is not a cell-surface antigen, the cells were treated with a perforation solution (0.05% Triton X-100, 1% BSA, 0.1 M Phosphate buffered saline, pH 7.2) for 5 minutes. Then, the cells were reacted with the primary antibodies for 30 minutes, and reacted with the fluorescent labeled secondary antibodies for 30 minutes, followed by washing with the phosphate buffer. Analysis was performed by FACScan (BD Bioscience, USA) using Cell Quest pro program (BD Bioscience). The primary antibodies used are as follows: mouse anti-human nestin antibody (1:50, Chemicon), mouse anti-tubulin antibody (1:50, Chemicon), and rabbit anti-human TH antibody (1:200, Pel-Freez). The secondary antibodies, which were used for fluorescent labeling of the primary antibodies, are as follows: Alexa Fluor 488 donkey anti-mouse IgG and Alexa Fluor 594 donkey anti-rabbit IgG (1:200, Molecular Probes).

Example 8

Transplantation in Animal Model for Functional Analysis and Validation

Figure 9:
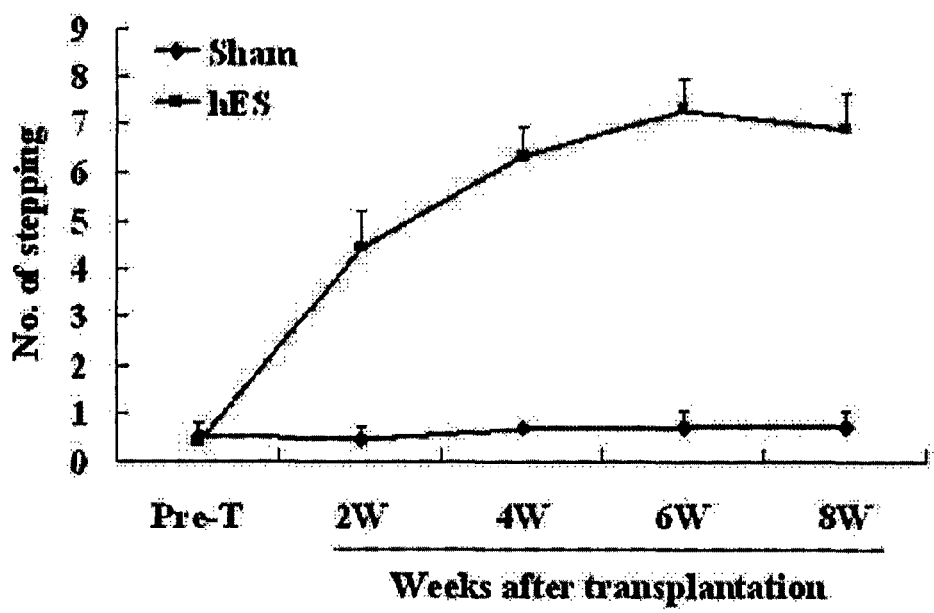
FIG. 9 is a drawing showing the result of a stepping test, in order to confirm whether the dopaminergic neurons derived from human embryonic stem cells can recover the function of the lesioned brain after transplantation in Parkinsonian animal models.
Figure 10:
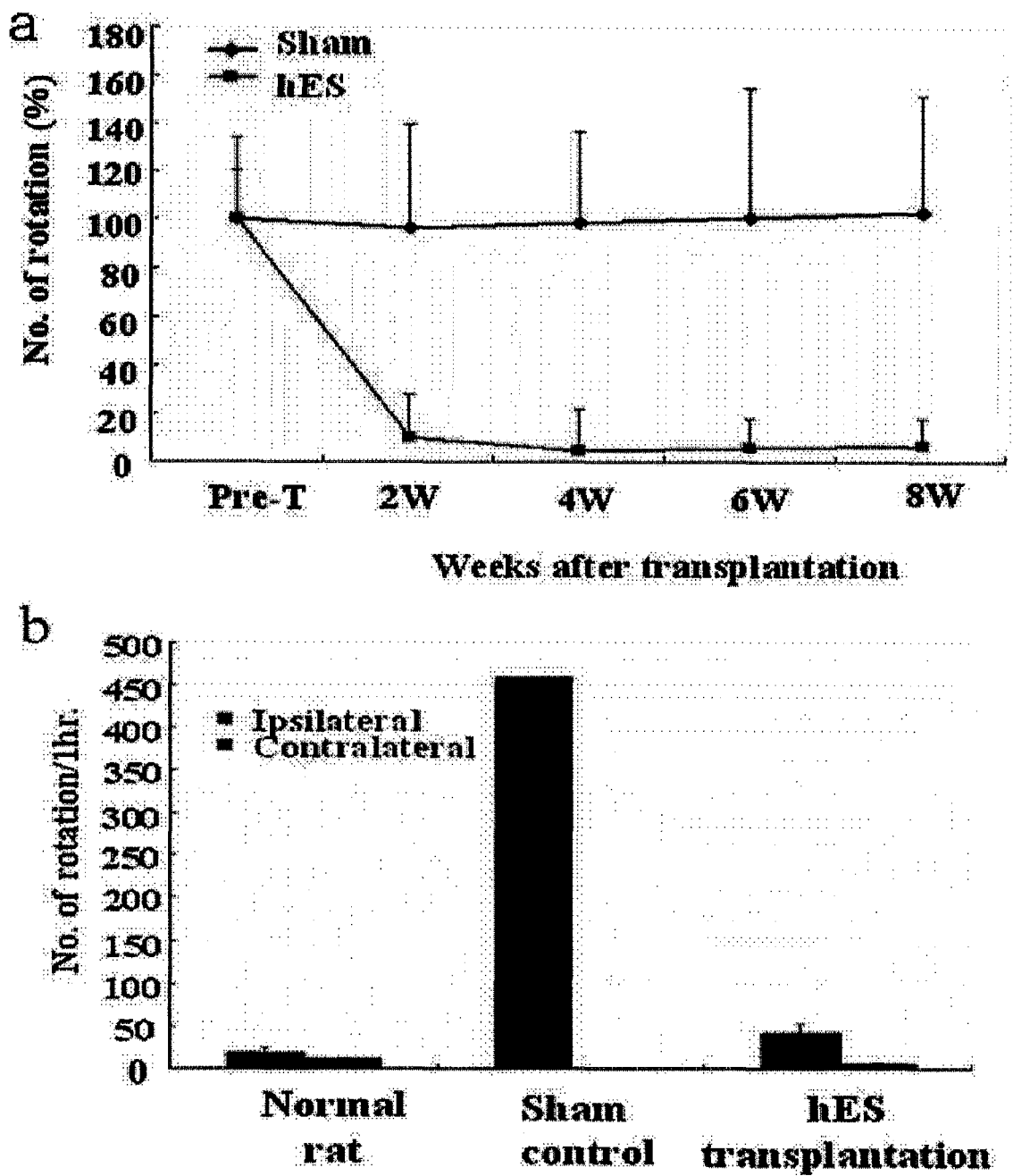
FIG. 10 is a drawing showing the result of a drug-induced turning behavior test, in order to confirm whether the dopaminergic neurons derived from human embryonic stem cells can recover the function of the lesioned brain after transplantation in Parkinsonian animal models (rat), in which a in FIG. 10 is the result of treating with apomorphine, and b in FIG. 10 is the result of treating with amphetamine. The drugs induce one direction of rotation in the dopamine-lesioned animal model, and if the cell therapy is effective, the number of rotations is reduced. Y axis is a value expressed as a percentage of rotations, based on the values obtained from the pre time point (the number of rotations in the animal model before transplantation).

Male Sprague-Dawley rats with an initial weight of 200 to 230 g were used to prepare Parkinsonian rat models. Experimental groups were divided into the following three groups: (i) a normal group, (ii) a sham control group of Parkinsonian rat models being not treated with the differentiated cells, (iii) a group of Parkinsonian rat models being treated with the differentiated cells from embryonic stem cells. In order to generate the Parkinsonian rat model, a neurotoxin 6-hydroxydopamine (6-OHDA) hydrobromide (8 μg free base in 2 μl of a solution containing 0.2% ascorbic acid) was injected into the medial forebrain bundle (MFB) according to the following stereotaxic coordinates: MFB; A-P (anterior-posterior)-4.4 mm, M-L (medial-lateral) 1.2 mm relative to bregma, and D-V (dorsal-ventral)-7.8 mm from the dura mater (38). To prevent the destruction of noradrenergic neurons, desipramine (12.5 mg/kg, i.p.) was administered 30 min prior to the injection of 6-OHDA. Two weeks after the development of 6-OHDA-induced lesions, the animals were tested for apomorphine (dopamine receptor agonist)-induced turning behavior (0.1 mg/kg i.p. in saline containing ascorbic acid at 2 mg/ml). One week after behavioral testing, human embryonic stem cell-derived neurons were prepared with accutase, and transplanted using a sterilized stainless steel needle (0.3 mm O.D.) connected to a Hamilton microsyringe. 4 μl of the cell suspension (1×10$^5$ cells/μl) was injected into the ipsilateral striatum [AP; +0.2 mm, M-L; 3.0 mm, D-V; 4.5 mm (2 μl) and 5.5 mm (2 μl)] over a period of 4 min. A time lapse of 4 min before the removal of the needle allowed the cells to settle down. The rats were given an injection of cyclosporin A (CsA: 10 mg/kg, i.p.) 24 hr before grafting. Cyclosporin A treatments were then continued in the rats until killed. For behavioral test, a forepaw adjusting stepping test (FIG. 9, Chang J W., et al. Biochemical and anatomical characterization of forepaw adjusting steps in rat models of Parkinson's disease: studies on medial forebrain bundle and striatal lesions. Neuroscience. 1999 88:617-628) and a drug-induced turning behavioral test (FIG. 10, Cho Y H., et al. Dopamine neurons derived from embryonic stem cells efficiently induce behavioral recovery in a Parkinsonian rat model. Biochem. Biophys. Res. Commun. 2006 341:6-12) were conducted together. The tests were continued after the $2^{nd}$ $4^{th}$ $6^{th}$, and $8^{th}$ week post-transplantation (FIG. 9 and a in FIG. 10), and after the $9^{th}$ week post-transplantation, the amphetamine-induced turning behavior test (3 mg/kg i.p.) was conducted (b in FIG. 10). The models transplanted with the differentiated cells (hES) showed a significant improvement in stepping and reduction in rotation number, as compared with the sham control group transplanted with only the medium.

From the results (FIG. 9 and FIG. 10), it was found that the differentiated dopaminergic neurons induced by the method of the invention and transplanted in the lesioned brain of the Parkinsonian rat model could recover the brain function. Therefore, it can be seen that the dopaminergic neurons differentiated from human embryonic stem cells, which were induced by the method of the invention, are useful for treating Parkinson's disease.

In the present Example, the dopaminergic neurons differentiated from human embryonic stem cells by the method of the invention were transplanted for the purpose of treating Parkinson's disease, but are limited thereto, as long as the dopaminergic neurons are used for treating the brain and nervous system diseases by recovering the function of the lesioned brain.

Example 9

Histological Assessment for Analysis of the Survival of Transplanted Dopaminergic Neurons Ten weeks after transplantation, the animals were anesthetized with 25% urethane in PBS and intracardially perfused with 125 ml of normal saline followed by 250 ml of ice-cold 4% paraformaldehyde. The brain of each rat was taken out, postfixed in the 4% paraformaldehyde solution, cryoprotected with 30% sucrose for 48 hours, and frozen. The brains were cut with a thickness of 30 μm to prepare tissue samples. The brain sections were incubated with primary antibodies, rabbit anti-tyroxine hydroxylase (TH), rabbit anti-βIII-tubulin, mouse anti-human nuclei or mouse anti-human mitochondria at 4° C. for 12 hours. As secondary antibodies, Alexa Fluor® 594 donkey anti-rabbit IgG and Alexa Fluor® 488 donkey anti-mouse IgG were incubated with the samples. Cells were mounted in a mounting solution containing 4',6-745 diamidino-2 phenylindole (DAPI), and observed under a confocal microscope (FIG. 11).

Figure 11:
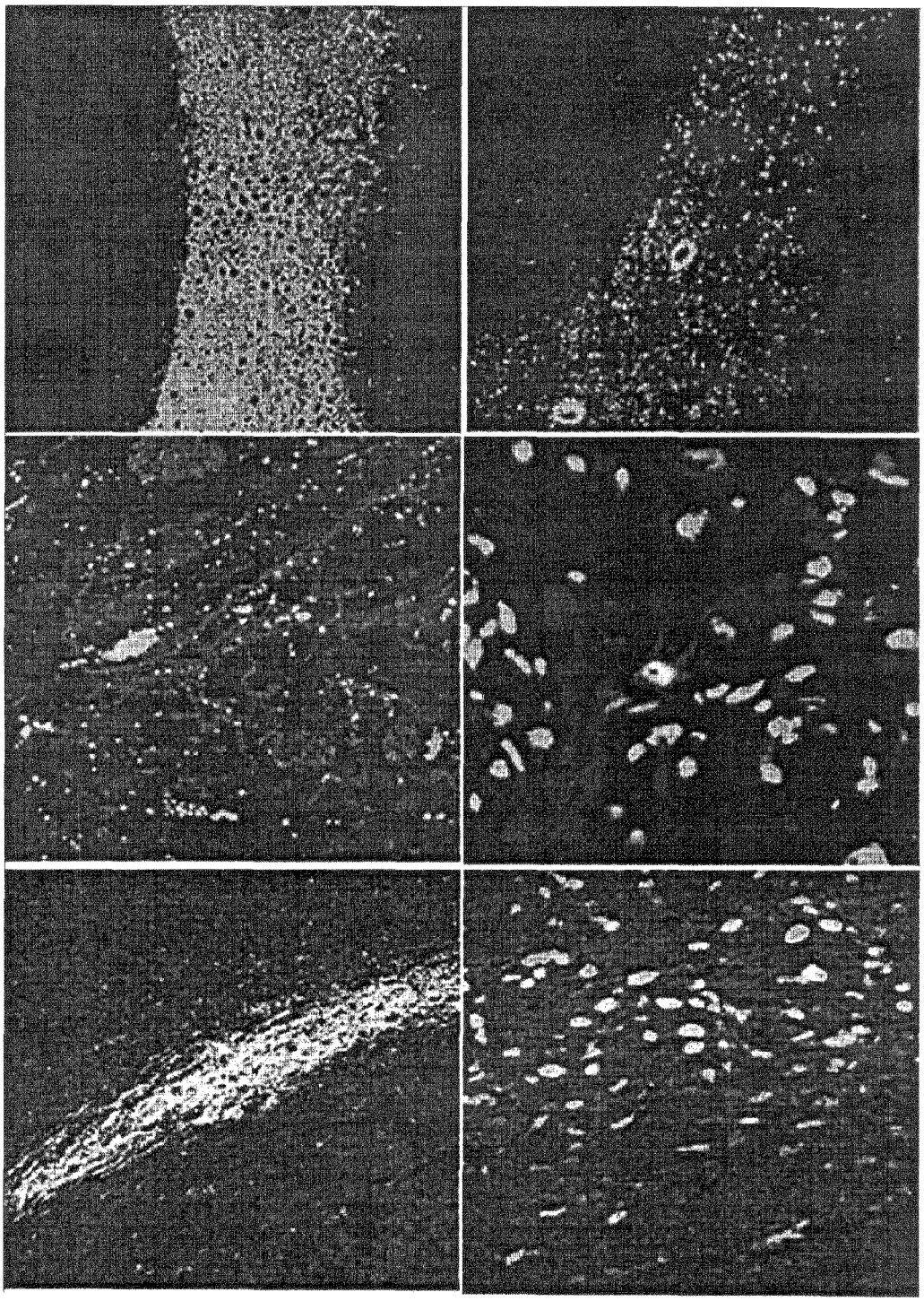
FIG. 11 is a photograph showing the result of immunofluorescence assay, in which the differentiated dopaminergic neurons from human embryonic stem cells are still alive and express specific markers of dopaminergic neurons, even after transplantation in the brain of Parkinsonian animal model.

Consequently, it was found that the cells having human-specific mitochondria and nuclei, that is, the transplanted cells survive well (a and b in FIG. 11), and most of them express the neuronal marker, βIII-tubulin (e and f in FIG. 11) and the dopaminergic neuronal marker, tyrosine hydroxylase (TH) (c and d in FIG. 11).

Based on the above results, it can be seen that the differentiated dopaminergic neurons induced by the method of the invention survive well even after transplantation, and express the antibodies specific to the dopaminergic neurons, thereby being useful for treating Parkinson's disease.

INDUSTRIAL APPLICABILITY

A method of the invention can differentiate the embryonic stem cells into the functional dopaminergic neurons under the suitable conditions. Therefore, it can be used as a cell replacement therapy for Parkinson's disease by replacing damaged dopaminergic neurons causing Parkinson's disease. Further, the method can be used for treating other brain and nervous system diseases by maintaining neural progenitors in the form of spherical neural mass, and offers a possibility of producing a large amount of neural progenitors and dopaminergic neurons within a relatively short time period.

The invention claimed is:

1. A method of producing spherical neural masses from human embryonic stem cells, comprising the steps of:
 (a) culturing human embryonic stem cells for 5 to 21 days to obtain embryoid bodies and removing cystic embryoid bodies having hollow ball morphology from the embryoid bodies;
 (b) attaching the resultant embryoid bodies to the surface of a culture dish coated with Matrigel, laminin, or L-polyornithine, and culturing them in media containing 0.5× N-2 supplement for 5 to 7 days to inhibit the growth of cells other than neural progenitors;
 (c) culturing the resultant culture for 3 to 7 days in media containing N-2 and bFGF;
 (d) dissecting and isolating neural structures having neural rosette or neural tube morphology from the resultant culture in step (c);
 (e) culturing in suspension the neural structures in media containing N-2 and bFGF to obtain spherical neural masses, wherein the spherical neural masses have expanded neural structures and spherical morphology, and express Nestin, Sox1 and Pax6;
 (f) removing spot-forming fibroblast-like cells and cystic structures, which are generated during step (e), and isolating only the expanded neural structures in the spherical neural masses; and
 (g) repeating step (e) and step (f) at least four times to increase a purity of the spherical neural masses and expand the spherical neural masses.

2. The method according to claim 1, wherein the media in steps (a), (b) and (c) are DMEM/F12 media containing at least one of 2 mM L-glutamine, 1% non essential amino acid, 0.5% penicillin-streptomycin (P/S), and 0.1 mM β-mercaptoethanol, excluding serum or serum replacement.

3. The method according to claim 2, wherein the media in steps (a), (b) and (c) are DMEM/F12 media containing 0.1 mM β-mercaptoethanol.

4. The method according to claim 1, wherein the method for dissecting and isolating in step (d) is a mechanical method using a glass Pasteur pipette.

5. The method according to claim 1, wherein step (e) and step (f) are repeated 4 to 10 times in step (g).

* * * * *

UNITED STATES PATENT AND TRADEMARK OFFICE
CERTIFICATE OF CORRECTION

PATENT NO. : 8,492,149 B2
APPLICATION NO. : 12/303670
DATED : July 23, 2013
INVENTOR(S) : Cho et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this
Eighth Day of September, 2015

Michelle K. Lee
*Director of the United States Patent and Trademark Office*